United States Patent
Francisco, Jr. et al.

[19]

[11] Patent Number: 5,974,858
[45] Date of Patent: Nov. 2, 1999

[54] SINGLE FLANGE INSTALLATION DENSIMETER

[75] Inventors: Edward E. Francisco, Jr., Paradise Valley; Gary D. Cohrs, Scottsdale, both of Ariz.

[73] Assignee: Calibron Systems, Inc., Scottsdale, Ariz.

[21] Appl. No.: 09/071,730

[22] Filed: May 1, 1998

Related U.S. Application Data

[60] Provisional application No. 60/045,480, May 2, 1997.

[51] Int. Cl.⁶ .................................................. G01N 9/00
[52] U.S. Cl. ............................................................ 73/32 A
[58] Field of Search .............................. 73/32 A, 24.05, 73/863.51, 863.58

[56] References Cited

U.S. PATENT DOCUMENTS

| | | | |
|---|---|---|---|
| 2,956,431 | 10/1960 | Westerheim | 73/32 |
| 3,385,104 | 5/1968 | Banks | 73/67.2 |
| 3,444,723 | 5/1969 | Wakefield | 73/32 |
| 3,585,843 | 6/1971 | Stansfeld | 73/32 |
| 4,018,089 | 4/1977 | Dzula et al. | 73/863.58 |
| 4,354,377 | 10/1982 | Stansfeld | 73/32 A |
| 4,466,272 | 8/1984 | Stansfeld | 73/32 A |
| 4,679,947 | 7/1987 | Miller et al. | 73/32 A |
| 4,962,671 | 10/1990 | Stansfeld et al. | 73/861.37 |
| 5,129,263 | 7/1992 | Chi | 73/861.38 |
| 5,253,533 | 10/1993 | Lam et al. | 73/861.37 |
| 5,287,754 | 2/1994 | Kazakis | 73/861.38 |
| 5,323,658 | 6/1994 | Yao et al. | 73/861.37 |
| 5,365,794 | 11/1994 | Hussain et al. | 73/861.37 |
| 5,381,697 | 1/1995 | van der Pol | 73/861.37 |
| 5,834,657 | 11/1998 | Clawson et al. | 73/863.51 |

OTHER PUBLICATIONS

Krohne America Inc., "CORIMASS G–Series—The new mass flowmeter from Krone," Sep. 1994, 8pp.
Schlumberger, "Solartron™ Type 7827 Viscometer" brochure, 3 pp. (undated).

*Primary Examiner*—John E. Chapman
*Attorney, Agent, or Firm*—Christie, Parker & Hale, LLP

[57] ABSTRACT

A densimeter is provided that is mounted on the side of a conduit carrying a fluid flow. The densimeter consists of an inlet and an outlet scoop which are immersed into the fluid flow through the conduit. A portion of the fluid flow enters into the first scoop and is directed into the densimeter where the fluid's density is measured and then exits through the exit scoop back into the fluid flow in the conduit.

16 Claims, 2 Drawing Sheets

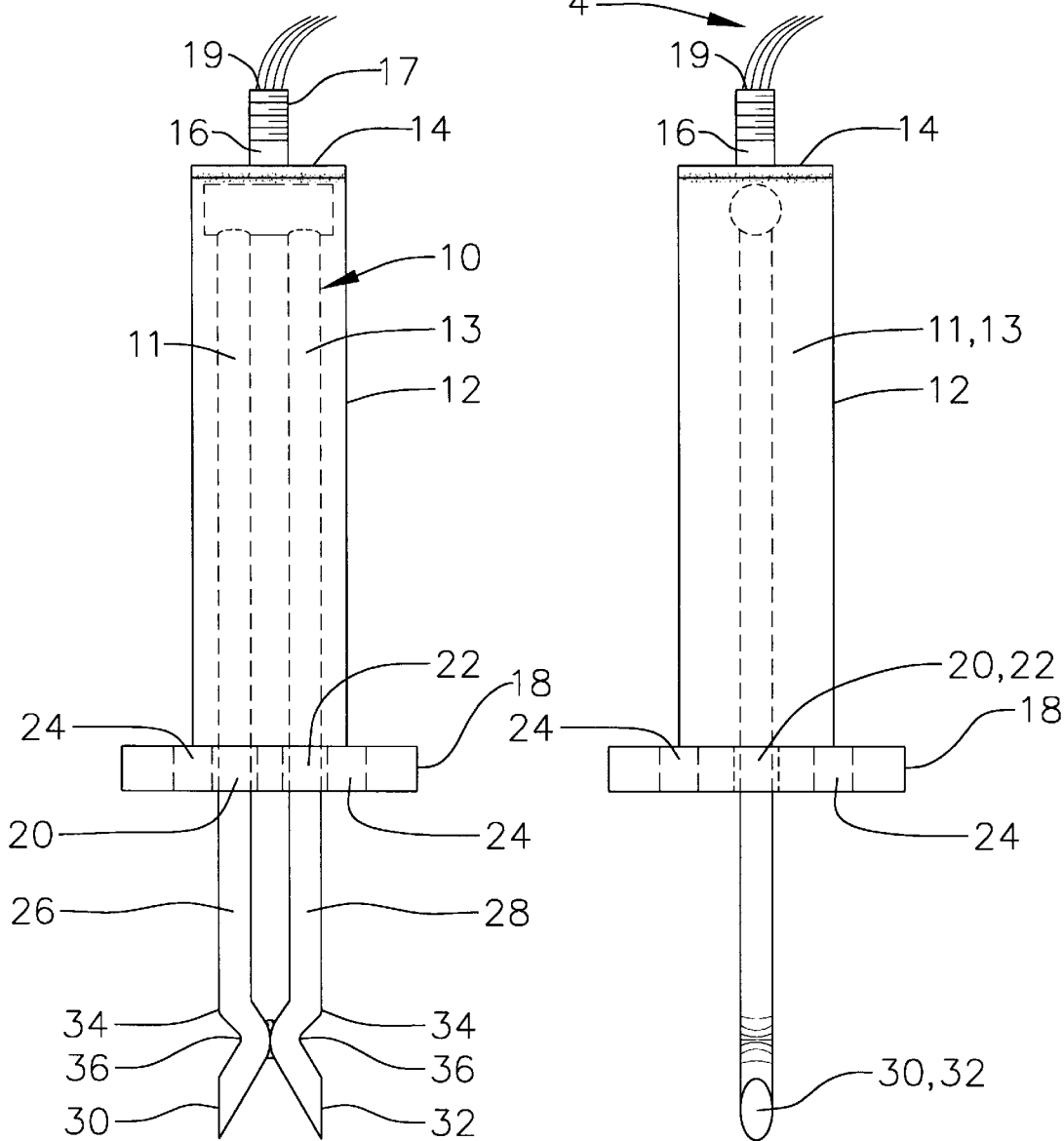
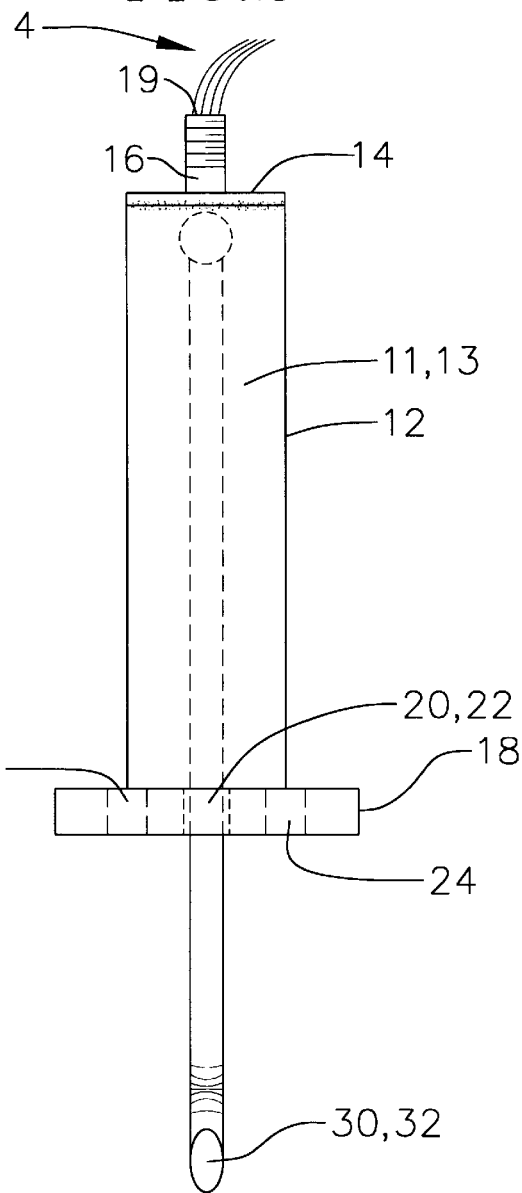
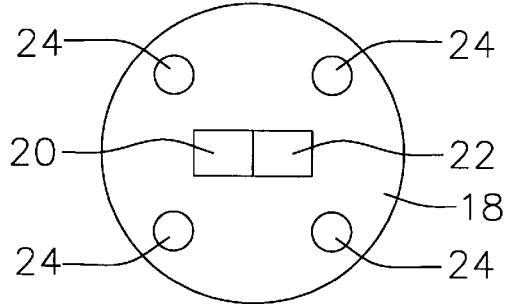

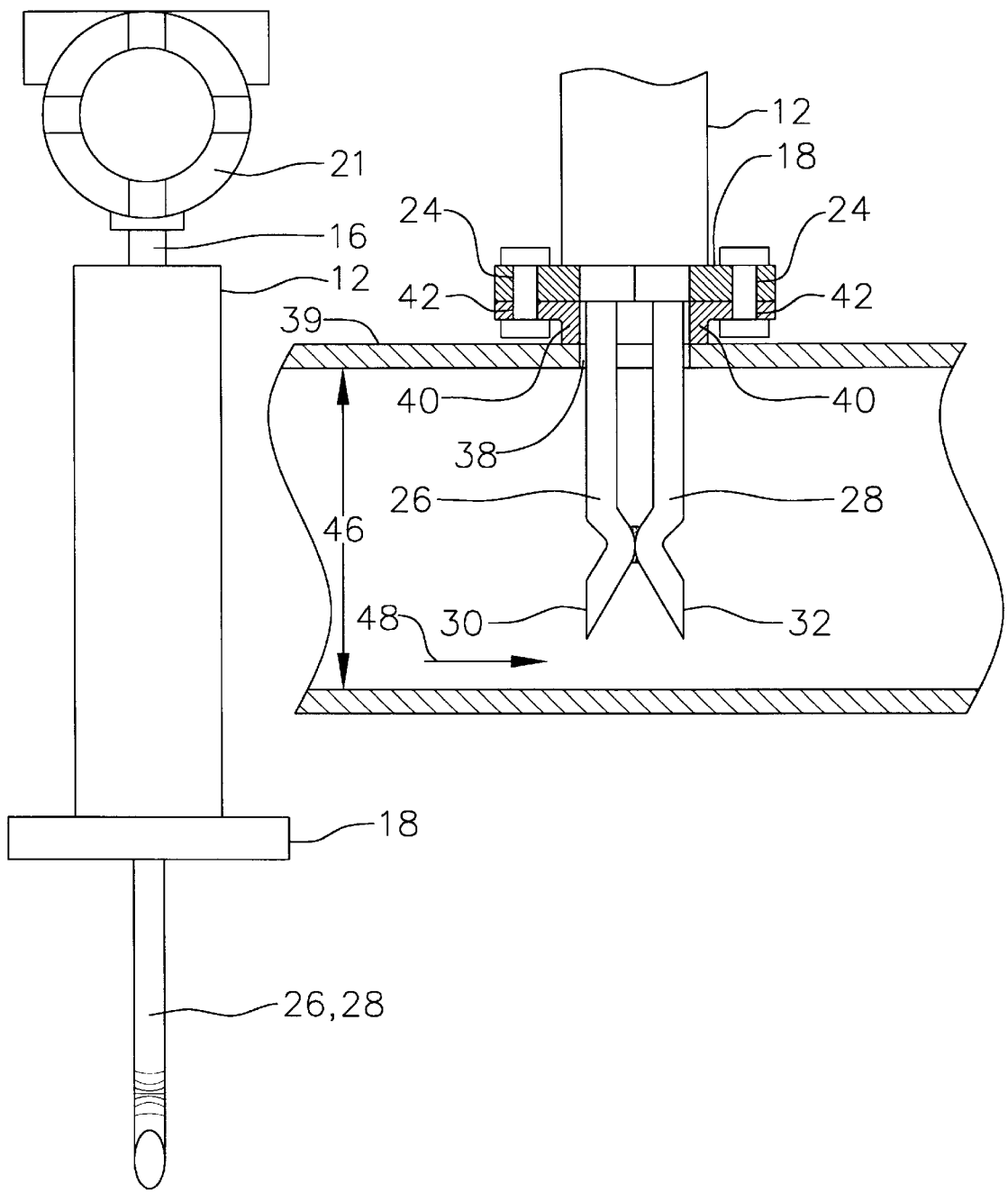

5,974,858

SINGLE FLANGE INSTALLATION DENSIMETER

CROSS REFERENCE TO RELATED APPLICATION

This application is based upon and claims priority pursuant to 35 U.S.C. §119(e) and 37 C.F.R. §1.78(a)(4) to Provisional Application Ser. No. 60/045,480, filed May 2, 1997.

BACKGROUND OF THE INVENTION

This invention relates to a densimeter and more specifically to a densimeter that can be mounted on a pipeline or other conduit carrying a fluid stream for measuring the density of the fluid.

A typical densimeter consists of a U-shaped vibrating tube having two ends and a driving force unit. The drive force unit maintains the tube's natural vibration through an electrical feedback driving circuit and supplies an output signal of the same frequency as the tube vibration. This response frequency is inversely related to the fluid's density. Thus, the density of the fluid can be calculated based on this response frequency. A temperature sensor, preferably a resistance temperature detector (an RTD sensor), is attached directly to one of the tube's end. The sensor supplies temperature information for making corrections to the measurements. The vibrating tube is calibrated for density, temperature and pressure and specific coefficients are developed which need to be used for the purpose of calculating the density of the fluid.

The U-shaped tube is housed in a casing. Two elbow shaped tubes extends from each end of the tube and extend beyond the casing. The measure of the fluid flow through the pipeline is "broken," i.e., divided into two sections. The first elbow of the densimeter is connected to the upstream section while the other elbow is connected to the downstream section of the pipeline. Thus, fluid from the upstream end of the pipeline flows through the densimeter and into the downstream section of the pipeline. The disadvantage with this type of densimeter is that it requires that the pipeline be broken, i.e., it is designed for in-line installation.

As such, there is a requirement of a densimeter that can be mounted on a pipeline without the need for breaking the pipeline.

SUMMARY OF THE INVENTION

A densimeter and a method for using such a densimeter is provided that can be easily installed and removed from a conduit or pipeline carrying fluid for measuring the density of the fluid. The densimeter consists of a vibrating U-tube which is housed in a casing. A flange is formed at the bottom of the housing. A scoop extends from each end of the U-tube and penetrates beyond the housing and flange. An opening is formed on the side of the conduit or pipeline. A flange is formed surrounding the opening. The densimeter housing flange is mated to the flange surrounding the opening and fastened together. The scoops penetrate into the conduit through the opening and are immersed into the fluid flow. One of the scoops faces upstream of the fluid flow while the other faces downstream. As fluid flows through the conduit, a portion of it flows into the scoop facing upstream and is directed into the vibrating U-tube where the fluid's density is measured. The fluid then continues out through the scoop facing downstream and back into the fluid flow in the pipeline or conduit. In essence, the densimeter of the present invention samples the fluid flow through the pipeline or conduit and measures its density.

BRIEF DESCRIPTION OF THE DRAWINGS

FIG. 1 is a side view of the densimeter of the present invention.

FIG. 2 is a side view of the densimeter shown in FIG. 1 rotated 90° away from the side shown in FIG. 1.

FIG. 3 is a bottom view of the flange which is used for mounting the densimeter onto a pipe.

FIG. 4 is a side view of the densimeter with an electrical connector mounted on the top of the densimeter housing.

FIG. 5 is a partial cross-sectional view depicting a densimeter of the present invention mounted on a pipeline carrying a fluid stream.

DETAILED DESCRIPTION OF THE INVENTION

A typical densimeter consists of a spring mass system containing a vibrating tube flooded with a fluid to be measured. The natural frequency of the vibrating tube is affected by the density of the measured fluid. The typical densimeter is designed for in-line installation, i.e., the unit is installed in line to a pipeline through which travels the fluid whose density is to be measured. The disadvantage with in line densimeter is that the pipeline must be "broken", i.e., taken apart, in order to install, service, or remove the densimeter.

The present invention densimeter allows for easy installation and removal from a pipeline or other conduit. The terms pipeline, pipe and conduit are used herein interchangeably. The present invention consists of a densimeter which has a highly accurate small, light weight, vibrating U-tube 10. The U-tube has two vibrating legs 11, 13 (FIGS. 1 and 2). The vibrating tube is typically made from a Hastelloy alloy 276, with the remaining wetted parts and the flange made from the 316 stainless steel. The U-tube is encased in a housing conduit 12.

The time period for vibration of the tube legs depends upon the natural frequency of the legs and the density of the product contained in the legs. The output signal, as in other vibrating tube densimeters, is slightly non-linear and requires correction for temperature.

A high pressure cover 14 is welded on top of the housing conduit. The cover is made from 304 stainless steel. The cover has a small opening to allow for the passage of wires which are connected to the various sensors and actuators incorporated on the U-tube. The sensors and actuators used are typically piezoelectric devices (not shown). A nipple 16 is typically welded on the top of the cover opening. The nipple also has a central opening 19 which is aligned with the cover small opening to allow for the passage of the wires. The nipple preferably also has outer threads 17. An electrical conector 21 having internal threads, preferably conforming to the national pipe thread (NPT) standard and matched to the nipple outer threads 17 is typically threaded on the nipple threads (FIG. 4). The cover with nipple and threaded electrical connector prevent any condensation from forming inside the housing conduit which could impair the densimeter performance.

A signal processor, preferably a SPUD Model 620 processor, and transmitter are mounted internally on the housing conduit for processing and transmitting signals indicative of density. Other comparable transmitters and processors may also be used. Signal amplification circuitry, as well as a temperature sensor are also mounted internally on the conduit. A preferred temperature sensor is a 100 ohm RTD temperature sensor with a 4–20 ma output.

A flange 18 is welded to the bottom of the housing conduit 12. The flange has two central openings 20,22 to provide access to the vibrating U-tube ends. Four holes 24 are formed on the periphery of the flange end are typically equidistant from each other, as shown in FIG. 3, which depicts a bottom view of the flange.

The housing conduit 12 with welded cover and flange provide for an explosion proof shield to the vibrating U-tube. In this regard, if the vibrating tube were to rupture, no injury, damage, product loss or other hazard will result.

Scoops 26, 28 are aligned with the ends of the legs of the U-tube through openings 20, 22 in the flange. Each scoop is a tube which is bent to form a scoop. Each tube has two open ends. The first open end is aligned with an open end of a leg of the U-tube. Each scoop first open end may be directly connected to the open end of a U-tube leg through the flange or may be connected to the flange and aligned to the open end of a U-tube leg. Each scoop second open end forms a scooping end opening, 30, 32.

To form the scoop, an end of the tube end is bent at two locations. At a first location 34, the tube is bent in one direction, and in a second location 36, which is closer to the scooping end opening, the tube is bent in the opposite direction preferably between 90° and 180°. The scoops extend from the flange such that their scooping end openings 30, 32 are opposite each other. Moreover, the outer surfaces of the two scoops opposite the bend along the second bending location 36 are attached to each other, preferably by welding, to make the structure more rigid Typically, this is accomplished by a quarter inch long bead weld.

An opening 38 is typically formed on the pipeline 39 which carries the fluid whose density is to be measured (FIG. 5). A pipeline flange 40 is typically welded or otherwise formed over the opening 38 on the pipeline. The flange 40 also has openings 42 matched to the openings 24 on the densimeter flange 18. To install the densimeter, the densimeter flange 18 is mated against the pipeline flange 40 and fastened together through openings 24 and 42. When so installed, scoops 26, 28 extend into the flow path of the fluid in pipeline 39 with one of the scoop end openings facing upstream while the other is facing downstream. As such, a portion of the fluid flow is scooped by the upstream facing scoop and guided through the densimeter U-tube where its density is measured finally exiting through the scoop facing downstream back into the fluid stream. As such, the scoops serve as a probe to sample a portion in this fluid for density measuring purposes.

As will become apparent to one skilled in the art, the length of scoops 26 and 28 is driven by the diameter 46 of the pipeline. The scoops must be long enough so that when the densimeter is connected to the pipeline, the scooping end openings 30, 32 are immersed in the fluid flow through the pipeline. Once connected to the pipeline, a portion of the fluid enters the first scoop opening 30 and travels through the vibrating U-tube 10 and exits through the second scoop opening 32. To ease the entry and exit of fluid through the scoops, it is preferred that the scoop open ends 30 and 32 are each formed along a plane that is perpendicular to the fluid flow 48 through the pipeline. This requires that opening 30 faces upstream to sample the fluid passing through pipeline 39 and opening 32 faces downstream to permit the fluid to return to pipeline 39 in a streamlined manner. To facilitate inflow and outflow from the scoops, their openings 30, 32 are formed along a plane that is oblique relative to a longitudinal axis of each tube that forms a scoop. In this regard, the openings 30, 32 are elliptical in cross-section as can be seen from FIGS. 1 and 2, and thus, their major diameter is larger than the diameter of the tube forming each scoop. This increase in the opening area allows for increased flow rates through the densimeter.

We claim:

1. A densimeter for measuring, through an opening on the side of a conduit, the density of a fluid carried in the conduit, the densimeter comprising:

a tube capable of vibrating for measuring the density of a fluid passing through the tube;

a first scoop forming an inlet and extending from a first end of the tube for immersing in the fluid stream by penetrating the conduit through the opening; and a second scoop forming an outlet and extending from a second end of the tube for penetrating the conduit through the opening; and a casing for housing the tube, wherein the scoops extend beyond the casing, wherein each scoop comprises a pipe bent at a first location in a first direction and at a second location in a direction opposite the first direction.

2. A densimeter for measuring through an opening on the side of a conduit, the density of a fluid carried in the conduit, the densimeter comprising:

a tube capable of vibrating for measuring the density of a fluid passing through the tube;

a first scoop forming an inlet and extending from a first end of the tube for immersing in the fluid stream by penetrating the conduit through the opening; and a second scoop forming an outlet and extending from a second end of the tube for penetrating the conduit through the opening; and a casing for housing the tube, wherein the scoops extend beyond the casing, wherein each scoop comprises a pipe section bent forming an angle greater than 90° and less than 180°.

3. A densimeter as recited in claim 2 wherein each scoop comprises a pipe section bent a first location in a first direction and at a second location in a direction opposite the first direction.

4. A densimeter as recited in claim 2 wherein the first scoop faces opposite the second scoop.

5. A densimeter as recited in claim 2 further comprising a flange at the end of the casing for mounting onto a side of the conduit.

6. A densimeter as recited in claim 2 wherein the first scoop comprises an opening formed along a plane wherein when immersed into the fluid stream the plane is perpendicular to the fluid flow.

7. A densimeter as recited in claim 6 wherein the second scoop is immersed into the fluid stream and wherein the second scoop comprises an opening formed along a plane wherein when immersed into the fluid stream the plane of the second scoop is perpendicular to the fluid flow.

8. A system for measuring the density of a fluid comprising:

a conduit carrying the fluid flow;

an opening formed on a side of the conduit;

a casing coupled to the opening;

a densimeter tube capable of vibrating for measuring the density of a fluid passing through it, the densimeter tube housed in the casing;

an inlet tube having an inlet opening and extending from a first end of the densimeter tube beyond the casing and into the fluid flow wherein the inlet opening faces upstream and wherein the inlet opening is formed along an inlet plane wherein the inlet plane is oblique relative to an inlet tube longitudinal axis; and an outlet tube having an outlet opening and extending from a second end of the densimeter tube beyond the casing and into the fluid flow wherein the outlet opening faces downstream.

9. A system as recited in claim 8 further comprising:

a conduit flange surrounding the opening; and a housing flange at a base of the housing penetrated by the inlet and outlet, wherein the housing flange is connected to the conduit flange for coupling the housing to the conduit.

10. A system as recited in claim 8 wherein the inlet tube forms a scoop for scooping a least a portion of the fluid flow through the conduit.

11. A system as recited in claim 8 wherein the inlet opening is perpendicular to the fluid flow.

12. A system as recited in claim 8 wherein the outlet opening is formed along an outlet plane wherein the outlet plane is oblique relative to the outlet tube longitudinal axis.

13. A system as recited in claim 12 wherein the outlet opening is perpendicular to the fluid flow.

14. A method for measuring the density of a fluid flowing through a conduit using a densimeter comprising the steps of:

forming an opening on the conduit;

providing a densimeter comprising an inlet tube having an opening for the inflow of fluid and an outlet having an opening for the outflow of fluid; and immersing at least a portion of the inlet opening and at least a portion of the outlet opening into the fluid flow through the conduit opening, wherein the inlet opening faces upstream, wherein the inlet opening is formed along a plane oblique to the longitudinal axis of the inlet tube, and wherein the outlet opening faces downstream and wherein fluid flow enters the inlet opening and travels through the densimeter where the fluid density is measured and exists through the outlet opening.

15. A method as recited in claim 14 wherein the inlet opening is formed along a plane and wherein the step of immersing the comprises the step of immersing the inlet opening into the fluid flow such that the plane is perpendicular to the fluid flow.

16. A method as recited in claim 15 wherein the outlet opening is formed along an outlet plane, the method comprising the step of immersing the outlet opening into the fluid flow such that the outlet plane is perpendicular to the fluid flow.

* * * * *